United States Patent
Kato et al.

(10) Patent No.: US 10,040,316 B2
(45) Date of Patent: *Aug. 7, 2018

(54) RUBBER COMPOSITION FOR TIRE TREAD, AND STUDLESS TIRE

(71) Applicant: THE YOKOHAMA RUBBER CO., LTD., Minato-ku, Tokyo (JP)

(72) Inventors: Manabu Kato, Hiratsuka (JP); Ryota Takahashi, Hiratsuka (JP); Takahiro Okamatsu, Hiratsuka (JP); Yoshiaki Kirino, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/565,373

(22) PCT Filed: Apr. 12, 2016

(86) PCT No.: PCT/JP2016/061799
§ 371 (c)(1),
(2) Date: Oct. 9, 2017

(87) PCT Pub. No.: WO2016/167248
PCT Pub. Date: Oct. 20, 2016

(65) Prior Publication Data
US 2018/0072102 A1   Mar. 15, 2018

(30) Foreign Application Priority Data

Apr. 13, 2015 (JP) ................. 2015-081858

(51) Int. Cl.
| | |
|---|---|
| B60C 1/00 | (2006.01) |
| C08C 19/22 | (2006.01) |
| B60C 11/00 | (2006.01) |
| C07C 251/32 | (2006.01) |
| C08K 5/33 | (2006.01) |
| C08L 9/00 | (2006.01) |
| C08K 9/10 | (2006.01) |
| C08L 15/00 | (2006.01) |

(52) U.S. Cl.
CPC ........ B60C 1/0016 (2013.01); B60C 11/0008 (2013.01); C07C 251/32 (2013.01); C08C 19/22 (2013.01); C08K 5/33 (2013.01); C08K 9/10 (2013.01); C08L 9/00 (2013.01); C08L 15/00 (2013.01)

(58) Field of Classification Search
CPC .................................. C08C 19/22; C08L 15/00
See application file for complete search history.

(56) References Cited

U.S. PATENT DOCUMENTS

| | | | |
|---|---|---|---|
| 3,792,031 A | 2/1974 | Udding | |
| 7,485,684 B2 * | 2/2009 | Parker | B60C 1/0016 152/564 |
| 9,493,599 B2 * | 11/2016 | Takahashi | C08F 236/10 |
| 9,493,637 B2 * | 11/2016 | Maejima | C08C 19/34 |
| 9,701,761 B2 * | 7/2017 | Takahashi | C08C 19/22 |
| 9,757,982 B2 * | 9/2017 | Kato | B60C 1/0016 |
| 9,790,353 B2 * | 10/2017 | Takahashi | C08L 21/00 |
| 9,873,749 B2 * | 1/2018 | Kato | C08L 7/00 |
| 2006/0148979 A1 | 7/2006 | Mori et al. | |

FOREIGN PATENT DOCUMENTS

| | | |
|---|---|---|
| JP | 48-016996 A | 3/1973 |
| JP | 2005-120183 A | 5/2005 |
| JP | 2007-039499 A | 2/2007 |
| JP | 2010-185025 A | 8/2010 |
| JP | 2012-012435 A | 1/2012 |
| JP | 2012-211316 A | 11/2012 |
| JP | 2013-224361 A | 10/2013 |
| WO | 2012/144605 A1 | 10/2012 |
| WO | WO-2014077364 A1 * | 5/2014 ............. C08C 19/22 |

* cited by examiner

*Primary Examiner* — Vickey M Nerangis
(74) *Attorney, Agent, or Firm* — Carrier Blackman & Associates, P.C.; Joseph P. Carrier; William D. Blackman

(57) ABSTRACT

The present invention is to provide a rubber composition for a tire tread, which can produce a studless tire having both excellent performance on ice and excellent wear resistance, and to provide a studless tire using the rubber composition. The rubber composition for a tire tread of the present invention contains 100 parts by mass of a diene rubber (A) containing a modified butadiene rubber and from 0.5 to 25 parts by mass of thermally expandable microcapsules (B). The modified butadiene rubber is obtained by modifying an unmodified butadiene rubber with a carboxy group-containing nitrone compound. The content of the modified butadiene rubber in the diene rubber (A) is from 20 to 65 mass %.

20 Claims, 1 Drawing Sheet

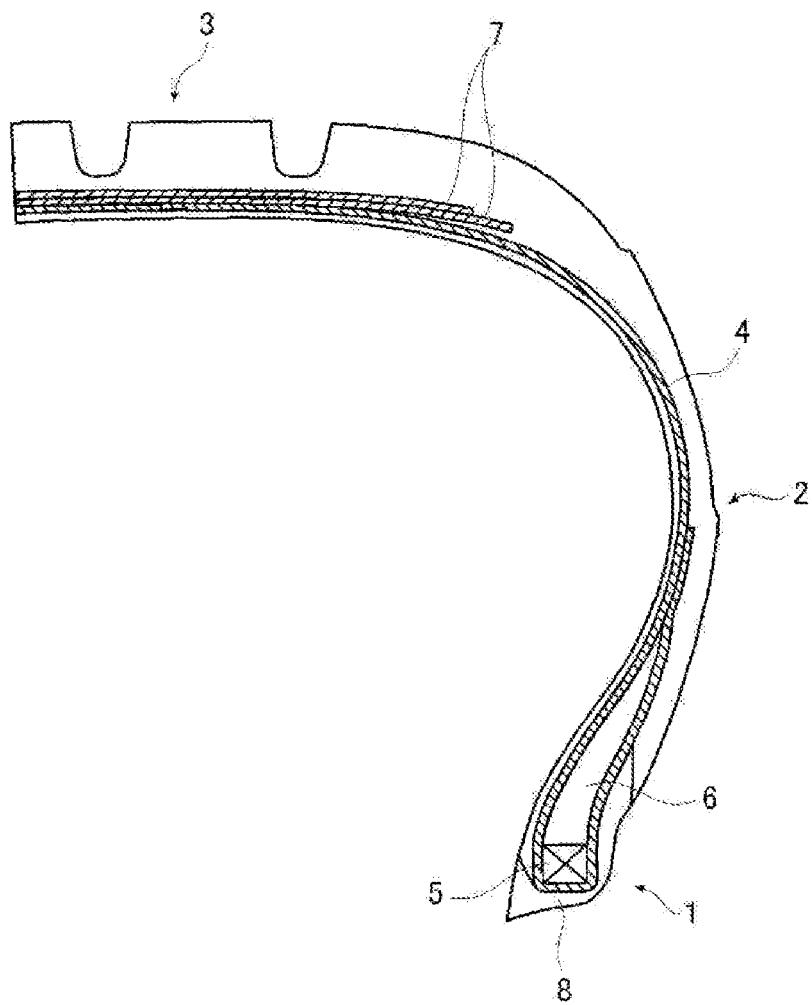

RUBBER COMPOSITION FOR TIRE TREAD, AND STUDLESS TIRE

TECHNICAL FIELD

The present invention relates to a rubber composition for a tire tread, and a studless tire.

BACKGROUND ART

Conventionally, to enhance friction on ice of studless tires, rubber compositions for tires containing thermally expandable microcapsules have been developed.

For example, Patent Document 1 discloses "a rubber composition for a tire tread, for a tire bead filler, or for a reinforcing liner of a run flat tire, the rubber composition comprising 100 parts by weight of a diene rubber and 0.5 to 25 parts by weight of a heat expandable microcapsule composed of a thermoplastic resin particle having a substance enclosed therein, the substance being capable of vaporizing or expanding due to heat to thereby generate a gas, wherein a shell of the heat expandable microcapsule comprises a thermoplastic resin obtained by polymerization of a nitrile-based monomer (I) as a main component of a monomer, a monomer (II) having an unsaturated double bond and carboxyl group in the molecule thereof, a monomer (III) having two or more polymerizable double bonds and, optionally, a copolymerizable monomer (IV) for adjusting expansion characteristics".

CITATION LIST

Patent Literature

Patent Document 1: JP 2005-120183 A

SUMMARY OF INVENTION

Technical Problem

However, when the inventors of the present invention studied a rubber composition containing thermally expandable microcapsules and a diene rubber referring to the composition described in Patent Document 1, it was found that, when the composition is used in a studless tire, wear resistance may be poor although excellent performance on ice is achieved.

Therefore, an object of the present invention is to provide a rubber composition for a tire tread, which can produce a studless tire having both excellent performance on ice and excellent wear resistance, and to provide a studless tire using the rubber composition.

Solution to Problem

As a result of diligent research to solve the problem described above, the present inventors found that a studless tire having both excellent performance on ice and excellent wear resistance can be produced by blending a modified butadiene rubber in which an unmodified butadiene rubber is modified with a carboxy group-containing nitrone compound, and thus completed the present invention.

Specifically, the inventors found that the problem described above can be solved by the following features.

[1]
A rubber composition for a tire tread, the rubber composition containing:

100 parts by mass of a diene rubber (A) containing a modified butadiene rubber, and from 0.5 to 25 parts by mass of thermally expandable microcapsules (B);

the modified butadiene rubber being obtained by modifying an unmodified butadiene rubber with a carboxy group-containing nitrone compound; and a content of the modified butadiene rubber in the diene rubber (A) being from 20 to 65 mass %.

[2]
The rubber composition for a tire tread according to [1] above, further containing:

from 0.3 to 30 parts by mass of a crosslinkable oligomer or polymer (C) not compatible with the diene rubber (A), and from 0.1 to 12 parts by mass of three-dimensionally crosslinked microparticles (D) having an average particle diameter of 1 to 200 μm.

[3]
The rubber composition for a tire tread according to [2] above, where the microparticles (D) are microparticles in which an oligomer or polymer (d1) not compatible with the crosslinkable oligomer or polymer (C) is three-dimensionally crosslinked.

[41]
The rubber composition for a tire tread according to [2] or [3] above, where the crosslinkable oligomer or polymer (C) is a polyether-based, polyester-based, polyolefin-based, polycarbonate-based, aliphatic, saturated hydrocarbon-based, acrylic, or plant-derived polymer or copolymer.

[5]
The rubber composition for a tire tread according to [3] or [4] above, where the oligomer or polymer (d1) is a polycarbonate-based, aliphatic, saturated hydrocarbon-based, acrylic, or plant-derived polymer or copolymer.

[6]
The rubber composition for a tire tread according to [4] or [5] above, where the crosslinkable oligomer or polymer (C) is a polyether-based, polyester-based, polyolefin-based, polycarbonate-based, acrylic, or plant-derived polymer or copolymer, and the oligomer or polymer (d1) is an aliphatic polymer or copolymer.

[7]
The rubber composition for a tire tread according to any one of [1] to [6] above, where the carboxy group-containing nitrone compound is a compound selected from the group consisting of N-phenyl-α-(4-carboxyphenyl)nitrone, N-phenyl-α-(3-carboxyphenyl)nitrone, N-phenyl-α-(2-carboxyphenyl)nitrone, N-(4-carboxyphenyl)-α-phenylnitrone, N-(3-carboxyphenyl)-α-phenylnitrone, and N-(2-carboxyphenyl)-α-phenylnitrone.

[8]
The rubber composition for a tire tread according to any one of [1] to [7] above, where, when a proportion (mol %) of double bonds modified with the carboxy group-containing nitrone compound among all the double bonds derived from butadiene contained in the unmodified butadiene rubber is a degree of modification, the degree of modification of the modified butadiene rubber is from 0.02 to 4.0 mol %.

[9]
The rubber composition for a tire tread according to any one of [1] to [8] above, where an amount of the carboxy group-containing nitrone compound used during the modification of the unmodified butadiene rubber is from 0.3 to 10 parts by mass per 100 parts by mass of the unmodified butadiene rubber.

[10]

A studless tire including the rubber composition for a tire tread described in any one of [1] to [9] above in a tire tread portion.

Advantageous Effects of Invention

As described below, according to the present invention, a rubber composition for a tire tread, which can produce a studless tire having both excellent performance on ice and excellent wear resistance, and a studless tire using the rubber composition can be provided.

BRIEF DESCRIPTION OF DRAWING

FIG. 1 is a schematic, partial cross-sectional view of a tire that represents an embodiment of the studless tire of the present invention.

DESCRIPTION OF EMBODIMENTS

The rubber composition for a tire tread and the studless tire using the rubber composition of the present invention are described below.

Note that, in the present invention, numerical ranges indicated using "(from) . . . to . . . " include the former number as the lower limit value and the later number as the upper limit value.

Rubber Composition for Tire Tread

The rubber composition for a tire tread of the present invention (hereinafter, simply referred to as "rubber composition") contains 100 parts by mass of a diene rubber (A) containing a modified butadiene rubber and from 0.5 to 25 parts by mass of thermally expandable microcapsules (B). Furthermore, the modified butadiene rubber is obtained by modifying an unmodified butadiene rubber with a carboxy group-containing nitrone compound. Furthermore, the content of the modified butadiene rubber in the diene rubber (A) is from 20 to 65 mass %.

The rubber composition of the present invention can produce a studless tire having both excellent performance on ice and excellent wear resistance. Although the details of the reason thereof is not clear, it is surmised that the following is a part of the reason.

That is, the rubber composition of the present invention contains a modified butadiene rubber obtained by modifying an unmodified butadiene rubber with a carboxy group-containing nitrone compound.

By this, it is conceived that the carboxy group of the nitrone modification moiety in the modified butadiene rubber interacts with other components in the rubber composition (in particular, carbon black, a white filler described below, and the like). As a result, due to the increase in crosslinking moieties by the formation of firm bonds between the rubber component and the other components, it is conceived that crosslinking density increases and wear resistance is enhanced.

Furthermore, at a high temperature, bonding between the rubber component and the other components due to the interaction described above is eliminated. As a result, since the viscosity of the rubber composition decreases, effect on foaming process of the thermally expandable microcapsules can be reduced. By this, it is conceived that the function of enhancing performance on ice due to the thermally expandable microcapsules can be sufficiently exhibited.

The components contained in the rubber composition of the present invention are described in detail below.

Diene Rubber (A)

There are no particular restrictions to the diene rubber contained in the rubber composition of the present invention as long as it contains from 20 to 65 mass % of the modified butadiene rubber described below and has double bonds in the main chain thereof. Specific examples thereof include natural rubbers (NR), isoprene rubbers (IR), unmodified butadiene rubbers, acrylonitrile-butadiene rubbers (NBR), styrene-butadiene rubbers (SBR), styrene-isoprene rubbers (SIR), styrene-isoprene-butadiene rubbers (SIBR), and the like. One type of these may be used alone, or two or more types of these may be used in combination.

Among these, as the diene rubber used in combination with the modified butadiene rubber described below, natural rubbers (NR), isoprene rubbers (IR), and styrene-butadiene rubbers (SBR) are preferable, and natural rubbers (NR) are more preferable.

Modified Butadiene Rubber

The modified butadiene rubber contained in the rubber composition of the present invention is a modified polymer obtained by modifying an unmodified butadiene rubber with a carboxy group-containing nitrone compound.

The content of the modified butadiene rubber in the diene rubber (A) is from 20 to 65 mass %, preferably from 30 to 65 mass %, and more preferably from 50 to 60 mass %. When the content of the modified butadiene rubber is within the range described above, excellent performance on ice and excellent wear resistance can be achieved. On the other hand, when the content of the modified butadiene rubber is less than 20 mass %, wear resistance is reduced. Furthermore, when the content of the modified butadiene rubber is greater than 65 mass %, sufficient rubber strength cannot be maintained.

Unmodified Butadiene Rubber

The unmodified butadiene rubber described above is a butadiene rubber containing a carbon-carbon unsaturated bond.

Note that "unmodified" refers to a state that is not modified with the carboxy group-containing nitrone compound described below, and the word "unmodified" does not exclude polymers that have been modified with other components (especially, terminal-modified polymers).

The unmodified butadiene rubber described above is preferably a butadiene rubber with a high cis structure and, specifically, is more preferably a butadiene rubber with a cis-1,4 bond content of 90% or greater and preferably 95% or greater, because reduction effect of heat build-up is increased.

Note that such a butadiene rubber with a high cis structure can be polymerized by a typical method using a Ziegler catalyst, neodymium catalyst, or the like.

The unmodified butadiene rubber described above preferably has a weight average molecular weight of 50000 to 1000000, and more preferably 200000 to 800000. The weight average molecular weight (Mw) of the unmodified butadiene rubber is measured by gel permeation chromatography (GPC) using tetrahydrofuran as a solvent and based on calibration with polystyrene standard.

Carboxy Group-Containing Nitrone Compound

The modified butadiene rubber of the present invention is a substance modified using a carboxy group-containing nitrone compound (hereinafter, also simply referred to as "carboxynitrone") described above.

The carboxynitrone is not particularly limited as long as it is a nitrone that has at least one carboxy group (—COOH). The nitrone herein refers to a compound having a nitrone group represented by Formula (1) below.

[Chemical Formula 1]

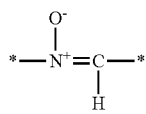

Formula (1)

In Formula (1) above, * indicates a bonding position.

The carboxynitrone is preferably a compound represented by the general formula (2) below.

[Chemical Formula 2]

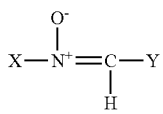

Formula (2)

In the general formula (2) above, X and Y each independently represent an aliphatic hydrocarbon group, an aromatic hydrocarbon group, or an aromatic heterocycle group that may have a substituent. However, at least one of X and Y has a carboxy group as a substituent.

Examples of the aliphatic hydrocarbon group represented by X or Y include alkyl groups, cycloalkyl groups, alkenyl groups, and the like. Examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, a 2-methylbutyl group, a 1,2-dimethylpropyl group, an n-hexyl group, an n-heptyl group, an n-octyl group, and the like. Among these, alkyl groups having from 1 to 18 carbons are preferable, and alkyl groups having from 1 to 6 carbons are more preferable. Examples of the cycloalkyl group include a cyclopropyl group, a cyclobutyl group, a cyclopentyl group, a cyclohexyl group, and the like. Among these, cycloalkyl groups having from 3 to 10 carbons are preferable, and cycloalkyl groups having from 3 to 6 carbons are more preferable. Examples of the alkenyl group include a vinyl group, a 1-propenyl group, an allyl group, an isopropenyl group, a 1-butenyl group, a 2-butenyl group, and the like. Among these, alkenyl groups having from 2 to 18 carbons are preferable, and alkenyl groups having from 2 to 6 carbons are more preferable.

Examples of the aromatic hydrocarbon group represented by X or Y include aryl groups, aralkyl groups, and the like.

Examples of the aryl group include a phenyl group, a naphthyl group, an anthryl group, a phenanthryl group, a biphenyl group, and the like. Among these, aryl groups having from 6 to 14 carbons are preferable, aryl groups having from 6 to 10 carbons are more preferable, and a phenyl group and a naphthyl group are even more preferable.

Examples of the aralkyl group include a benzyl group, a phenethyl group, a phenylpropyl group, and the like. Among these, aralkyl groups having from 7 to 13 carbons are preferable, aralkyl groups having from 7 to 11 carbons are more preferable, and a benzyl group is even more preferable.

Examples of the aromatic heterocycle group represented by X or Y include a pyrrolyl group, a furyl group, a thienyl group, a pyrazolyl group, an imidazolyl group (an imidazole group), an oxazolyl group, an isoxazolyl group, a thiazolyl group, an isothiazolyl group, a pyridyl group (a pyridine group), a furan group, a thiophene group, a pyridazinyl group, a pyrimidinyl group, a pyrazinyl group, and the like. Among these, a pyridyl group is preferable.

The group represented by X and Y may contain a substituent other than the carboxy group (hereinafter, also referred to as "other substituent") as long as the at least one of X or Y contains the carboxy group as the substituent as described above.

The other substituent contained in the group represented by X or Y are not particularly limited, and examples thereof include alkyl groups having from 1 to 4 carbons, hydroxy groups, amino groups, nitro groups, sulfonyl groups, alkoxy groups, halogen atoms, and the like.

Note that examples of the aromatic hydrocarbon group having such a substituent include aryl groups having a substituent, such as a tolyl group and a xylyl group; aralkyl groups having a substituent, such as a methylbenzyl group, an ethylbenzyl group, and a methylphenethyl group; and the like.

The compound represented by the general formula (2) above is preferably a compound represented by the general formula (b) below.

[Chemical Formula 3]

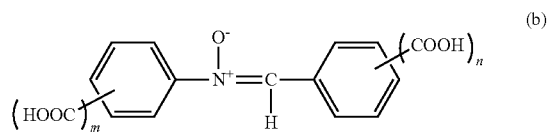

(b)

In the general formula (b), m and n each independently represent an integer of 0 to 5, and the sum of m and n is 1 or greater.

The integer represented by m is preferably an integer of 0 to 2, and more preferably an integer of 0 or 1, because solubility to a solvent during the carboxynitrone synthesis will be better and thus synthesis will be easier.

The integer represented by n is preferably an integer of 0 to 2, and more preferably an integer of 0 or 1, because solubility to a solvent during carboxynitrone synthesis will be better and thus synthesis will be easier. Furthermore, the sum of m and n (m+n) is preferably from 1 to 4, and more preferably 1 or 2.

The carboxynitrone represented by the general formula (b) is not particularly limited but is preferably a compound selected from the group consisting of N-phenyl-α-(4-carboxyphenyl)nitrone represented by Formula (b1) below, N-phenyl-α-(3-carboxyphenyl)nitrone represented by Formula (b2) below, N-phenyl-α-(2-carboxyphenyl)nitrone represented by Formula (b3) below, N-(4-carboxyphenyl)-α-phenylnitrone represented by Formula (b4) below, N-(3-carboxyphenyl)-α-phenylnitrone represented by Formula (b5) below, and N-(2-carboxyphenyl)-α-phenylnitrone represented by Formula (b6) below.

[Chemical Formula 4]

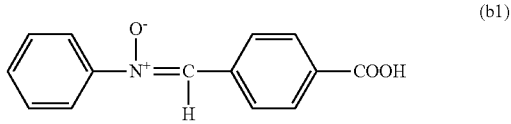

(b1)

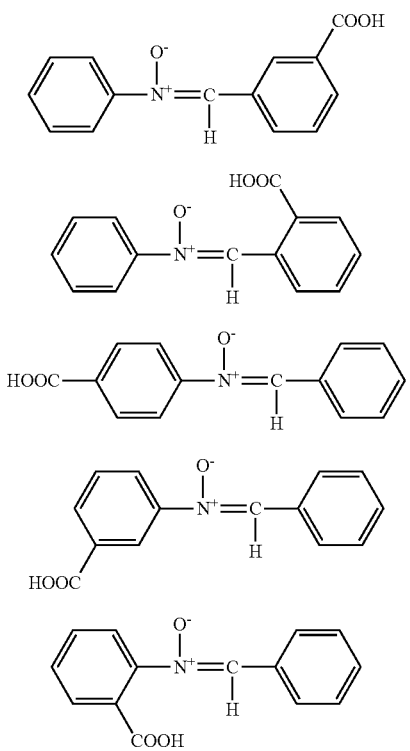

(b2), (b3), (b4), (b5), (b6)

The method of synthesizing the carboxynitrone is not particularly limited, and conventionally known methods can be used. For example, a compound (carboxynitrone) having a carboxy group and a nitrone group can be obtained by stirring a compound having a hydroxyamino group (—NHOH) and a compound having an aldehyde group (—CHO) and a carboxy group at a molar ratio of hydroxyamino groups to aldehyde groups (—NHOH/—CHO) of 1.0 to 1.5 in the presence of an organic solvent (for example, methanol, ethanol, and tetrahydrofuran) at room temperature for 1 to 24 hours to allow the both groups to react.

Method of Producing Modified Butadiene Rubber

The modified butadiene rubber of the present invention can be obtained by modifying an unmodified butadiene rubber with a carboxy group-containing nitrone compound, as described above.

The reaction mechanism during the production of the modified butadiene rubber is a mechanism in which a carboxynitrone is reacted with a double bond of an unmodified butadiene rubber. The method of producing the modified butadiene rubber (modified BR) is not particularly limited. Examples of the method include a method in which the unmodified butadiene rubber and the carboxynitrone are mixed at 100 to 200° C. for 1 to 30 minutes.

At this time, a cycloaddition reaction occurs between the double bond derived from the butadiene contained in the unmodified butadiene rubber and the nitrone group in the carboxynitrone, forming a five-membered ring as shown in Formula (4-1) and Formula (4-2) below. Note that Formula (4-1) below represents a reaction between a 1,4-bond and a nitrone group, and Formula (4-2) below represents a reaction between a 1,2-vinyl bond and a nitrone group. Formulas (4-1) and (4-2) illustrate the reactions for the case where the butadiene is 1,3-butadiene, but the same reaction leads to a formation of a five-membered ring even in the case where the butadiene is other than 1,3-butadiene.

[Chemical Formula 5]

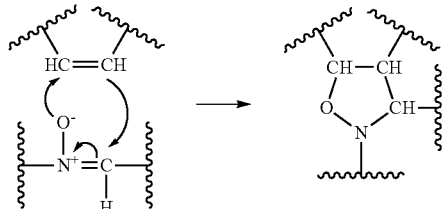

Formula (4-1)

[Chemical Formula 6]

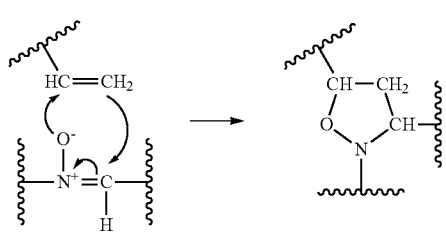

Formula (4-2)

The amount of the carboxynitrone used to modify the unmodified butadiene rubber (hereinafter, also referred to as "converted CPN amount") is preferably from 0.3 to 10 parts by mass, and more preferably from 0.3 to 3 parts by mass, per 100 parts by mass of the diene rubber (A). By setting the converted CPN amount to the range described above, the modification can be performed efficiently.

For example, if 35 parts by mass of the modified butadiene rubber is contained per 100 parts by mass of the diene rubber and the modified butadiene rubber is obtained via the reaction between 100 parts by mass of the unmodified butadiene rubber and 1 part by mass of carboxynitrone, since 0.35 parts by mass (=35×(1/101)) of carboxynitrone is used for synthesis of the modified butadiene rubber out of 35 parts by mass of the modified butadiene rubber, the converted CPN amount is 0.35 parts by mass.

The amount of the carboxynitrone used during the modification of the unmodified butadiene rubber (charged amount) is preferably from 0.3 to 10 parts by mass, and more preferably from 0.3 to 5 parts by mass, per 100 parts by mass of the unmodified butadiene rubber. By setting the charged amount of the carboxynitrone to the range described above, even better wear resistance is achieved.

The degree of modification of the modified butadiene rubber is preferably from 0.02 to 4.0 mol %, and more preferably from 0.10 to 2.0 mol %. Furthermore, the lower limit value of the degree of modification is preferably 0.20 mol % or greater.

Note that "degree of modification" represents the proportion (mol %) of the double bonds modified with the carboxynitrone relative to all the double bonds derived from the butadiene (butadiene unit) in the unmodified butadiene rubber. For example, if the butadiene is 1,3-butadiene, "degree of modification" represents the proportion (mol %) of the structure represented by Formula (4-1) above or Formula (4-2) above formed by modification with carboxynitrone. The degree of modification, for example, can be determined by NMR analysis of the BR before and after the modification.

Note that, in this specification, a modified butadiene rubber having a degree of modification of 100 mol % falls under the category of a diene rubber.

Thermally Expandable Microcapsules (B)

The rubber composition of the present invention contains thermally expandable microcapsules. The thermally expandable microcapsule is formed from a thermoplastic resin particle in which a substance that can be vaporized or expanded by heat to generate a gas is encapsulated. Note that the thermally expandable microcapsule becomes a microcapsule in which a gas is sealed inside the outer shell formed from a thermoplastic resin by heating at a temperature (e.g. 130 to 190° C.) equal to or higher than the initiation temperature of vaporization or expansion of the substance.

The particle diameter before the expansion of the thermally expandable microcapsules is preferably from 5 to 300 µm, and more preferably from 10 to 200 µm.

As the thermoplastic resin, for example, a polymer of (meth)acrylonitrile and/or a copolymer having a high (meth)acrylonitrile content can be suitably used. As other monomers (comonomer) in the case of the copolymer, a monomer, such as a halogenated vinyl, a halogenated vinylidene, a styrene-based monomer, a (meth)acrylate-based monomer, vinyl acetate, butadiene, vinyl pyridine, or chloroprene is used.

Note that the thermoplastic resin may be crosslinkable using a crosslinking agent, such as divinylbenzene, ethylene glycol di(meth)acrylate, triethylene glycol di(meth)acrylate, trimethylolpropane tri(meth)acrylate, 1,3-butylene glycol di(meth)acrylate, allyl(meth)acrylate, triacrylformal, or triallyl isocyanurate. Although the crosslinking condition is preferably an uncrosslinked condition, partial crosslinking may be allowed as long as the characteristics as a thermoplastic resin are not impaired.

Specific examples of the substance that generates a gas when vaporized or expanded by heat contained in the thermally expandable microcapsules include liquids such as hydrocarbons, such as n-pentane, isopentane, neopentane, butane, isobutane, hexane, and petroleum ether; and chlorinated hydrocarbons, such as methyl chloride, methylene chloride, dichloroethylene, trichloroethane, and trichloroethylene; or solids such as azodicarbonamide, dinitrosopentamethylenetetramine, azobisisobutyronitrile, toluenesulfonyl hydrazide derivatives, and aromatic succinyl hydrazide derivatives.

Commercially available products may be used as such thermally expandable microcapsules, and such thermally expandable microcapsules are available as, for example, trade names "Expancel 091DU-80" and "Expancel 092DU-120" manufactured by Expancel in Sweden, trade names "Matsumoto Microsphere F-85", "Matsumoto Microsphere F-100", and "Matsumoto Microsphere F-100D" manufactured by Matsumoto Yushi-Seiyaku Co., Ltd.

One type of these thermally expandable microcapsules may be used alone, or two or more types of these thermally expandable microcapsules may be used in combination.

In the present invention, the content of the thermally expandable microcapsules is from 0.5 to 25 parts by mass, and preferably from 1 to 10 parts by mass, per 100 parts by mass of the diene rubber (A). With the content of the thermally expandable microcapsules being within the range described above, excellent performance on ice can be achieved.

Crosslinkable Oligomer or Polymer (C)

The rubber composition of the present invention preferably contains a crosslinkable oligomer or polymer (C). By combined use of the crosslinkable oligomer or polymer (C) and the microparticles (D) described below, even better performance on ice is achieved.

The crosslinkable oligomer or polymer (C) is not particularly limited as long as the crosslinkable oligomer or polymer (C) is an oligomer or polymer that is not compatible with the diene rubber (A) described above and that has crosslinkability.

Note that "not compatible (with the diene rubber)" does not indicate the condition of being not compatible with all the rubber components contained in the diene rubber (A) but indicates the condition where specific components used in the diene rubber (A) and the crosslinkable oligomer or polymer (C) are not compatible with each other.

Examples of the crosslinkable oligomer or polymer (C) include a polyether-based, polyester-based, polyolefin-based, polycarbonate-based, aliphatic, saturated hydrocarbon-based, acrylic, plant-derived polymer or copolymer, and the like.

Among these, from the perspective of suitably using an aliphatic polymer or copolymer (e.g. liquid diene polymer) as the oligomer or polymer (d1) described below, the crosslinkable oligomer or polymer (C) is preferably a polyether-based, polyester-based, polyolefin-based, polycarbonate-based, acrylic, or plant-derived polymer or copolymer.

Examples of the polyether-based polymer or copolymer include polyethylene glycol, polypropylene glycol (PPG), polypropylene triol, ethylene oxide/propylene oxide copolymers, polytetramethylene ether glycol (PTMEG), sorbitol-based polyol, and the like.

Furthermore, examples of the polyester-based polymer or copolymer include condensation products of low molecular weight polyhydric alcohols (e.g. ethylene glycol, diethylene glycol, and propylene glycol) and polybasic carboxylic acids (e.g. adipic acid, sebacic acid, terephthalic acid, and isophthalic acid) (condensed polyester polyol); lactone-based polyols; and the like.

Furthermore, examples of the polyolefin-based polymer or copolymer include polyethylene, polypropylene, ethylene propylene copolymers (EPR, EPDM), polybutylene, polyisobutylene, hydrogenated polybutadiene, and the like.

Furthermore, examples of the polycarbonate-based polymer or copolymer include substances obtained by transesterification reaction of polyol compounds (e.g. 1,6-hexanediol, 1,4-butanediol, and 1,5-pentanediol) and dialkyl carbonates, and the like.

Furthermore, examples of the acrylic polymer or copolymer include acrylic polyols; homopolymers of acrylates, such as acrylate, methyl acrylate, ethyl acrylate, butyl acrylate, and 2-ethylhexyl acrylate; acrylate copolymers formed by combining two or more types of these acrylates; and the like.

Furthermore, examples of the plant-derived polymer or copolymer include plant oils and fats, such as castor oil and soybean oil; various elastomers derived from polyester polyol or the like formed by modifying polylactic acid or the like; and the like.

In the present invention, from the perspective of achieving even better performance on ice of tires by allowing the molecules to be crosslinked, the crosslinkable oligomer or polymer (C) preferably contains at least one reactive functional group selected from the group consisting of a hydroxy group, a silane functional group, an isocyanate group, a (meth)acryloyl group, an allyl group, a carboxy group, an acid anhydride group, and an epoxy group.

Note that the silane functional group is also referred to as "a crosslinkable silyl group". Specific examples thereof include a hydrolyzable silyl group; a silanol group; functional groups in which a silanol group is substituted with an acetoxy group derivative, an enoxy group derivative, an oxime group derivative, an amine group derivative, or the like; and the like.

Among these functional groups, from the perspective of appropriately crosslinking the crosslinkable oligomer or polymer (C) during the processing of the rubber, and achieving even better performance on ice of a tire and even better wear resistance, a silane functional group, isocyanate group, acid anhydride group, or epoxy group is preferably contained. In particular, a hydrolyzable silyl group or isocyanate group is more preferably contained.

Note that specific examples of the hydrolyzable silyl group include alkoxysilyl groups, alkenyloxysilyl groups, acyloxysilyl groups, aminosilyl groups, aminoxysilyl groups, oximesilyl groups, amidosilyl groups, and the like.

Among these, from the perspective of achieving excellent balance between hydrolyzability and storage stability, an alkoxysilyl group is preferable. Specifically, an alkoxysilyl group represented by Formula (5) below is more preferable, and a methoxysilyl group or ethoxysilyl group is even more preferable.

[Chemical Formula 7]

(5)

In the formula, $R^1$ represents an alkyl group having from 1 to 4 carbons, $R^2$ represents a hydrogen atom or an alkyl group having from 1 to 4 carbons, and a represents an integer of 1 to 3. When a is 2 or 3, the plurality of $R^1$ may be the same or different. When a is 1, the plurality of $R^2$ may be the same or different.

Furthermore, the isocyanate group described above is an isocyanate group remaining after a hydroxy group of a polyol compound (e.g. polycarbonate-based polyol) is reacted with an isocyanate group of a polyisocyanate compound.

Note that the polyisocyanate compound is not particularly limited as long as the polyisocyanate compound contains two or more isocyanate groups in a molecule. Specific examples thereof include aromatic polyisocyanates, such as TDI (e.g. 2,4-tolylene diisocyanate (2,4-TDI) and 2,6-tolylene diisocyanate (2,6-TDI)), MDI (e.g. 4,4'-diphenylmethane diisocyanate (4,4'-MDI) and 2,4'-diphenylmethane diisocyanate (2,4'-MDI)), 1,4-phenylene diisocyanate, polymethylene polyphenylene polyisocyanate, xylylene diisocyanate (XDI), tetramethylxylylene diisocyanate (TMXDI), tolidine diisocyanate (TODI), 1,5-naphthalene diisocyanate (NDI), and triphenylmethane triisocyanate; aliphatic polyisocyanates, such as hexamethylene diisocyanate (HDI), trimethylhexamethylene diisocyanate (TMHDI), lysine diisocyanate, and norbornane diisocyanate (NBDI); alicyclic polyisocyanates, such as transcyclohexane-1,4-diisocyanate, isophorone diisocyanate (IPDI), bis(isocyanate methyl)cyclohexane ($H_6$XDI), and dicyclohexylmethane diisocyanate ($H_{12}$MDI); carbodiimide-modified polyisocyanates of these; isocyanurate-modified polyisocyanates of these; and the like.

Note that, in the present invention, when the crosslinkable oligomer or polymer (C) having a hydroxy group as a reactive functional group is used, it is preferable to crosslink a part or all of the crosslinkable oligomer or polymer (C) using an isocyanate compound or the like in advance before blending with the diene rubber (A), or to blend a crosslinking agent, such as an isocyanate compound, in the rubber in advance.

In the present invention, the reactive functional group is preferably contained at least at a terminal of the main chain of the crosslinkable oligomer or polymer (C), and when the main chain is a straight chain, 1.5 or more reactive functional groups are preferably contained, and 2 or more reactive functional groups are more preferably contained. On the other hand, when the main chain is branched, 3 or more reactive functional groups are preferably contained.

Furthermore, in the present invention, from the perspective of achieving excellent dispersibility with the diene rubber (A) and/or kneading processability of the rubber composition, and from the perspective of facilitating the adjustment of particle size and/or shape when the microparticles (D) described below are prepared in the crosslinkable oligomer or polymer (C), the weight average molecular weight or number average molecular weight of the crosslinkable oligomer or polymer (C) is preferably from 300 to 30000, and more preferably from 500 to 25000.

Note that the weight average molecular weight and number average molecular weight are both measured by gel permeation chromatography (GPC) based on calibration with polystyrene standard.

When the crosslinkable oligomer or polymer (C) is contained, the content thereof is preferably from 0.3 to 30 parts by mass, more preferably from 0.5 to 25 parts by mass, and even more preferably from 1 to 15 parts by mass, per 100 parts by mass of the diene rubber (A).

Microparticles (D)

The rubber composition of the present invention preferably contains three-dimensionally crosslinked microparticles (D) having an average particle diameter of 1 to 200 μm. As described above, by combined use of the crosslinkable oligomer or polymer (C) and the microparticles (D), even better performance on ice is achieved.

From the perspective of making the surface of the tire appropriately rough and achieving even better performance on ice, the average particle size of the microparticles (D) is preferably from 1 to 50 μm, and more preferably from 5 to 40 μm.

Note that the average particle size indicates the average value of the equivalent circle diameter measured using a laser microscope, and for example, can be measured by the laser diffraction scattering particle size distribution analyzer LA-300 (manufactured by Horiba, Ltd.), laser microscope VK-8710 (manufactured by Keyence Corporation), and the like.

When the microparticles (D) are contained, the content thereof is preferably from 0.1 to 12 parts by mass, more preferably from 0.3 to 10 parts by mass, and even more preferably from 0.5 to 10 parts by mass, per 100 parts by mass of the diene rubber (A).

By allowing a predetermined amount of the microparticles (D) to be contained, excellent performance on ice is achieved. It is conceived that the performance on ice is enhanced because the local strain is dispersed due to the elasticity of the microparticles (D) and thus stress is alleviated.

Furthermore, in the present invention, from the perspective of achieving even better performance on ice of a tire, the microparticles (D) are preferably microparticles in which the oligomer or polymer (d1) that is not compatible with the crosslinkable oligomer or polymer (C) is three-dimensionally crosslinked in advance in the crosslinkable oligomer or polymer (C). It is conceived that this is because the crosslinkable oligomer or polymer (C) functions as a solvent of the microparticles (D) and the dispersibility of the crosslinkable oligomer or polymer (C) and the microparticles (D) in the rubber composition is enhanced when these mixtures are compounded in the rubber composition.

Note that "not compatible (with the crosslinkable oligomer or polymer (C))" does not indicate the condition of being not compatible with all the components contained in the crosslinkable oligomer or polymer (C) but indicates the condition where specific components used in the crosslinkable oligomer or polymer (C) and the oligomer or polymer (d1) are not compatible with each other.

Examples of the oligomer or polymer (d1) include a polycarbonate-based, aliphatic, saturated hydrocarbon-based, acrylic, plant-derived polymer or copolymer, and the like.

Examples of the aliphatic polymer or copolymer include liquid diene polymers, such as polyisoprene, polybutadiene, and styrene-butadiene copolymer; chloroprene rubber; butyl rubber; nitrile rubber; modified products containing a partially hydrogenated product of these and/or a reactive functional group described below; and the like.

Furthermore, examples of the saturated hydrocarbon-based polymer or copolymer include hydrogenated polyisoprene, hydrogenated polybutadiene, ethylene propylene, epichlorohydrin, chlorinated polyethylene, chlorosulfonated polyethylene, hydrogenated nitrile rubber, polyisobutylene, acrylic rubber, and the like.

Furthermore, examples of the polycarbonate-based polymer or copolymer include substances obtained by transesterification reaction of polyol compounds (e.g. 1,6-hexanediol, 1,4-butanediol, and 1,5-pentanediol) and dialkyl carbonates, and the like.

Furthermore, examples of the acrylic polymer or copolymer include acrylic polyols; homopolymers of acrylates, such as acrylate, methyl acrylate, ethyl acrylate, butyl acrylate, and 2-ethylhexyl acrylate; acrylate copolymers formed by combining two or more types of these acrylates; and the like.

Furthermore, examples of the plant-derived polymer or copolymer include plant oils and fats, such as castor oil and soybean oil; various elastomers derived from polyester polyol or the like formed by modifying polylactic acid or the like; and the like.

Among these, the oligomer or polymer (d1) is preferably an aliphatic polymer or copolymer, and from the perspective of achieving even better performance on ice and wear resistance of a tire, a liquid diene polymer is more preferable.

Examples of commercially available product of the liquid polyisoprene include Kuraprene LIR-30 and Kuraprene LIR-50 (both manufactured by Kuraray Co., Ltd.), Poly ip (manufactured by Idemitsu Kosan Co., Ltd.), and the like.

Furthermore, examples of the liquid polybutadiene include a homopolymer type, such as Kuraprene LBR-305 (manufactured by Kuraray Co., Ltd.); a copolymer type of 1,2-bond butadiene and 1,4-bond butadiene, such as Poly bd (manufactured by Idemitsu Kosan Co., Ltd.); a copolymer type of ethylene, 1,4-bond butadiene, and 1,2-bond butadiene, such as Kuraprene L-SBR-820 (manufactured by Kuraray Co., Ltd.); and the like.

In the present invention, from the perspective of three-dimensionally crosslinking only the oligomer or polymer (d1) in the crosslinkable oligomer or polymer (C), the oligomer or polymer (d1) preferably contains at least one reactive functional group selected from the group consisting of a hydroxy group, silane functional group, isocyanate group, (meth)acryloyl group, allyl group, carboxy group, acid anhydride group, and epoxy group that is different from the reactive functional group contained in the crosslinkable oligomer or polymer (C) and that does not react with the reactive functional group contained in the crosslinkable oligomer or polymer (C).

Note that the silane functional group is also referred to as "a crosslinkable silyl group". Specific examples thereof include, similar to the silane functional group contained in the crosslinkable oligomer or polymer (C) described above, a hydrolyzable silyl group; silanol group; functional groups in which a silanol group is substituted with an acetoxy group derivative, enoxy group derivative, oxime group derivative, amine group derivative, or the like; and the like.

Note that, after the oligomer or polymer (d1) is three-dimensionally crosslinked, the crosslinkable oligomer or polymer (C) may contain the reactive functional group that is the same as the oligomer or polymer (d1) (e.g. carboxy group, and hydrolyzable silyl group), and the already contained functional group may be modified to form the reactive functional group that is the same as the oligomer or polymer (d1).

Among these functional groups, from the perspective of easily proceeding the three-dimensional crosslinking of the oligomer or polymer (d1), a hydroxyl group, silane functional group, carboxy group, or acid anhydride group is preferably contained, and a carboxy group or acid anhydride group is more preferably contained.

Examples of commercially available product of the liquid polyisoprene having a carboxy group include Kuraprene LIR-410 (isoprene-monomethyl maleate-modified isoprene copolymer; number average molecular weight: 25000, manufactured by Kuraray Co., Ltd.), and the like. Examples of commercially available product of the liquid polyisoprene having an acid anhydride group include Kuraprene LIR-403 (isoprene-maleic anhydride-modified isoprene copolymer; number average molecular weight: 34000, manufactured by Kuraray Co., Ltd.), and the like.

In the present invention, the reactive functional group is preferably contained at least at a terminal of the main chain of the oligomer or polymer (d1), and when the main chain is a straight chain, 1.5 or more reactive functional groups are preferably contained, and 2 or more reactive functional groups are more preferably contained. On the other hand, when the main chain is branched, 3 or more reactive functional groups are preferably contained.

Furthermore, in the present invention, from the perspective of making the particle size and the crosslinking density of the microparticles (D) appropriate and achieving even better performance on ice of a tire, the weight average molecular weight or number average molecular weight of the oligomer or polymer (d1) is not particularly limited, but is preferably from 1000 to 100000, and more preferably from 3000 to 60000.

Note that the weight average molecular weight or number average molecular weight is measured by gel permeation chromatography (GPC) based on calibration with polystyrene standard.

Method of Preparing Microparticles (D)

Examples of the method of preparing the microparticles (D) by three-dimensionally crosslinking the oligomer or polymer (d1) in the crosslinkable oligomer or polymer (C) include methods in which three-dimensional crosslinking is performed using the reactive functional group contained in the oligomer or polymer (d1). Specific examples thereof include methods in which the oligomer or polymer (d1)

containing the reactive functional group is reacted with at least one type of component (d2) selected from the group consisting of water, a catalyst, and a compound having a functional group that reacts with the reactive functional group, to form three-dimensional crosslink, and the like.

Note that the water of the component (d2) can be suitably used when the oligomer or polymer (d1) contains a hydrolyzable silyl group, isocyanate group, or acid anhydride group as a reactive functional group.

Furthermore, examples of the catalyst of the component (d2) include a condensation catalyst of a silanol group (silanol condensation catalyst), and the like.

Specific examples of the silanol condensation catalyst include dibutyltin dilaurate, dibutyltin dioleate, dibutyltin diacetate, tetrabutyl titanate, tin(I) octanoate, and the like.

Furthermore, examples of the compound having a functional group that reacts with the reactive functional group of the compound (d2) include hydroxy group-containing compounds, silanol compounds, hydrosilane compounds, diisocyanate compounds, amine compounds, oxazolidine compounds, enamine compounds, ketimine compounds, and the like.

The hydroxy group-containing compound can be suitably used when the oligomer or polymer (d1) contains an isocyanate group or acid anhydride group as a reactive functional group.

The molecular weight, backbone, and the like of the hydroxy group-containing compound are not limited as long as the hydroxy group-containing compound is a compound having at least two hydroxy groups in a molecule. Examples thereof include low molecular weight polyhydric alcohols, polyether polyols, polyester polyols, polycarbonate polyols, polycaprolactone polyols, other polyols, mixed polyols of these, and the like.

The silanol compound can be suitably used when the oligomer or polymer (d1) contains a silane functional group as a reactive functional group.

Specific examples of the silanol compound include tert-butyldimethylsilanol, diphenylmethylsilanol, silanol group-containing polydimethylsiloxanes, silanol group-containing cyclic polysiloxanes, and the like.

The hydrosilane compound is a compound having an SiH group and can be suitably used when the oligomer or polymer (d1) contains an allyl group as a reactive functional group.

Specific examples of the hydrosilane compound include 1,1,3,3-tetramethyldisiloxane, 1,3,5,7-tetramethyltetracyclosiloxane, 1,3,5,7,8-pentamethylpentacyclosiloxane, and the like.

The diisocyanate compound can be suitably used when the oligomer or polymer (d1) contains a hydroxy group as a reactive functional group.

Specific examples of the diisocyanate compound include aromatic polyisocyanates, such as TDI (e.g. 2,4-tolylene diisocyanate (2,4-TDI) and 2,6-tolylene diisocyanate (2,6-TDI)), MDI (e.g. 4,4'-diphenylmethane diisocyanate (4,4'-MDI) and 2,4'-diphenylmethane diisocyanate (2,4'-MDI)), 1,4-phenylene diisocyanate, polymethylene polyphenylene polyisocyanate, xylylene diisocyanate (XDI), tetramethylxylylene diisocyanate (TMXDI), tolidine diisocyanate (TODI), 1,5-naphthalene diisocyanate (NDI), and triphenylmethane triisocyanate; aliphatic polyisocyanates, such as hexamethylene diisocyanate (HDI), trimethylhexamethylene diisocyanate (TMHDI), lysine diisocyanate, and methyl norbornane diisocyanate (NBDI); and the like.

The amine compound can be suitably used when the oligomer or polymer (d1) contains an isocyanate group, carboxy group, acid anhydride group, epoxy group, or the like as a reactive functional group.

The molecular weight, skeleton, or the like of the amine compound is not limited as long as the amine compound is a compound having an amino group in a molecule. Examples thereof include primary amines, such as butylamine, hexylamine, octylamine, dodecylamine, oleylamine, cyclohexylamine, and benzylamine; secondary amines, such as dibutylamine; polyamines, such as diethylenetriamine, triethylenetetramine, guanidine, diphenylguanidine, and xylylenediamine; and the like.

The oxazolidine compound, the enamine compound, and the ketimine compound can be suitably used when the oligomer or polymer (d1) contains an isocyanate group, acid anhydride group, epoxy group, or the like as a reactive functional group.

Specifically, compounds that are conventionally known as latent curing agents can be used as these compounds. In particular, an oxazolidine compound and/or ketimine compound is preferably used.

The oxazolidine compound is not particularly limited as long as the oxazolidine compound is a compound having at least one oxazolidine ring, which is a saturated five-membered ring having an oxygen and a nitrogen, in a molecule. Specific examples thereof include N-hydroxyalkyloxazolidine, oxazolidine silyl ether, carbonate oxazolidine, ester oxazolidine, and the like.

As such an oxazolidine compound, commercially available products, such as Hardener OZ (ester oxazolidine, manufactured by Sumika Bayer Urethane Co., Ltd.), can also be used.

The ketimine compound is a compound that generates a primary amine as an active hydrogen group-containing compound by hydrolysis. Note that, in the present invention, a compound having a C=N bond (ketimine bond) derived from ketone or aldehyde and amine is referred to as "ketimine", the ketimine also includes aldimine having an —HC=N bond.

Examples of the ketimine include substances having a structure in which a carbon atom of branched structure or a carbon atom as a ring member is bonded at the α-position of at least one of the carbon atom and the nitrogen atom of the ketimine bond. Examples of the carbon atom as a ring member include a carbon atom constituting an aromatic ring and a carbon atom constituting an alicycle.

Specific examples of the ketimine include (1) ketimine which is a reaction product of polyamine and a carbonyl compound and (2) silicon-containing ketimine which is a reaction product of aminoalkoxysilane and a carbonyl compound.

As such a ketimine compound, commercially available products, such as jER cure H3 (manufactured by Mitsubishi Chemical Corporation) and KBE-9103 (manufactured by Shin-Etsu Chemical Co., Ltd.), can be also used.

In the present invention, a solvent can be used as necessary when the microparticles (D) are prepared by three-dimensionally crosslinking the oligomer or polymer (d1) in the crosslinkable oligomer or polymer (C).

Examples of the mode of use of the solvent include a mode where a plasticizer, diluent, and solvent that serves as a good solvent for the oligomer or polymer (d1) and serves as a poor solvent for the crosslinkable oligomer or polymer (C) are used, and/or a mode where a plasticizer, diluent, and solvent that serves as a good solvent for the crosslinkable oligomer or polymer (C) and serves as a poor solvent for the oligomer or polymer (d1) are used.

Specific examples of such a solvent include aliphatic hydrocarbons, such as n-pentane, isopentane, neopentane, n-hexane, 2-methylpentane, 3-methylpentane, 2,2-dimethylbutane, 2,3-dimethylbutane, n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, n-octane, and isooctane; alicyclic hydrocarbons, such as cyclopentane, cyclohexane, and methylcyclopentane; aromatic hydrocarbons, such as xylene, benzene, and toluene; terpene-based organic solvents, such as α-pinene, β-pinene, and limonene; and the like.

Furthermore, in the present invention, when the microparticles (D) are prepared by three-dimensionally crosslinking the oligomer or polymer (d1) in the crosslinkable oligomer or polymer (C), the microparticles (D) are preferably prepared by using additives, such as a surfactant, emulsifier, dispersing agent, and silane coupling agent.

Other Components

The rubber composition of the present invention preferably contains other components in addition to those described above. Examples of the other components include a carbon black and/or white fillers, silane coupling agents, and the like.

Carbon Black and/or White Filler

Carbon Black

Specific examples of the carbon black include furnace carbon blacks such as SAF, ISAF, HAF, FEF, GPE, and SRF, and one of these can be used alone, or two or more types can be used in combination.

Furthermore, in the carbon black, the CTAB adsorption specific surface area is preferably from 60 to 180 $m^2/g$, more preferably from 80 to 160 $m^2/g$, and even more preferably from 80 to 130 $m^2/g$, from the perspective of achieving even better wear resistance.

Note that the CTAB adsorption specific surface area is a value of the amount of n-hexadecyltrimethylammonium bromide adsorbed to the surface of carbon black measured in accordance with JIS K6217-3:2001 "Part 3: Method for determining specific surface area—CTAB adsorption method."

White Filler

Specific examples of the white filler are silica, calcium carbonate, magnesium carbonate, talc, clay, alumina, aluminum hydroxide, titanium oxide, calcium sulfate, and the like. One type of these may be used alone or two or more types of these may be used in combination.

Among these, silica is preferable from the perspective of achieving even better performance on ice of a tire.

Specific examples of the silica include wet silica (hydrous silicic acid), dry silica (silicic anhydride), calcium silicate, aluminum silicate, and the like. One type of these may be used alone or two or more types of these may be used in combination.

Among these, wet silica is preferable from the perspective of achieving even better performance on ice of a tire and further improving wear resistance.

In the silica, the CTAB adsorption specific surface area is preferably from 50 to 300 $m^2/g$, more preferably from 70 to 250 $m^2/g$, and even more preferably from 90 to 200 $m^2/g$, from the perspective of achieving excellent wet performance and rolling resistance of a tire.

Note that the CTAB adsorption specific surface area is a value of the amount of n-hexadecyltrimethylammonium bromide adsorbed to the surface of silica measured in accordance with JIS K6217-3:2001 "Part 3: Method for determining specific surface area—CTAB adsorption method."

In the present invention, the content of the carbon black and/or white filler is, in terms of the total amount of the carbon black and the white filler, from 30 to 100 parts by mass, preferably from 40 to 90 parts by mass, and even more preferably from 45 to 80 parts by mass, per 100 parts by mass of the diene rubber (A).

Furthermore, when the carbon black and the white filler are used in combination, the content of the white filler is preferably from 5 to 85 parts by mass, and more preferably from 15 to 75 parts by mass, per 100 parts by mass of the diene rubber (A).

Silane Coupling Agent

When the rubber composition of the present invention contains the white filler (especially silica) described above, the rubber composition preferably contains a silane coupling agent because it improves the reinforcing performance of the tire.

When the silane coupling agent is compounded, the content thereof is preferably from 0.1 to 20 parts by mass, and more preferably from 4 to 12 parts by mass, per 100 parts by mass of the white filler.

Specific examples of the above silane coupling agent include bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl) tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 3-trimethoxysilylpropyl benzothiazole tetrasulfide, 3-triethoxysilylpropyl benzothiazole tetrasulfide, 3-triethoxysilylpropyl methacrylate monosulfide, 3-trimethoxysilylpropyl methacrylate monosulfide, bis(3-diethoxymethylsilylpropyl)tetrasulfide, 3-mercaptopropyldimethoxymethylsilane, dimethoxymethylsilylpropyl-N,N-dimethylthiocarbamoyl tetrasulfide, dimethoxymethylsilylpropyl benzothiazole tetrasulfide, and the like. One of these examples can be used alone, or a combination of two or more can be used.

Among these, from the perspective of enhancing effect on reinforcing properties, use of bis-(3-triethoxysilylpropyl) tetrasulfide and/or bis-(3-triethoxysilylpropyl)disulfide is preferable. Specific examples thereof include Si69 (bis(3-triethoxysilylpropyl)tetrasulfide, manufactured by Evonik Degussa), Si75 (bis(3-triethoxysilylpropyl)disulfide, manufactured by Evonik Degussa), and the like.

Furthermore, the rubber composition of the present invention may contain, as such another component, various additives typically used in rubber compositions for tires, including a filler such as calcium carbonate; a vulcanizing agent such as sulfur; a sulfenamide-based, guanidine-based, thiazole-based, thiourea-based, or thiuram-based vulcanization accelerator; a vulcanization accelerator aid, such as zinc oxide and stearic acid; wax; aroma oil, an anti-aging agent; a plasticizer; and the like.

Method of Producing Rubber Composition

There are no particular restrictions to the method of producing the rubber composition of the present invention, and an example is the method whereby each of the abovementioned components is kneaded using a publicly known method and device (such as a Banbury mixer, kneader, or roll).

In addition, the rubber composition of the present invention can be vulcanized or crosslinked under conventionally known vulcanizing or crosslinking conditions.

Studless Tire

The studless tire of the present invention (hereinafter, also simply referred to as "tire of the present invention") is a studless tire that uses the rubber composition of the present invention described above in a tire tread.

FIG. 1 is a schematic, partial cross-sectional view of a tire that represents an embodiment of the studless tire of the present invention, but the tire of the present invention is not limited to the embodiment illustrated in FIG. 1.

In FIG. 1, reference sign 1 denotes a bead portion, reference sign 2 denotes a sidewall portion, and reference sign 3 denotes a tread portion formed from the rubber composition for a tire of the present invention.

In addition, a carcass layer 4, in which a fiber cord is embedded, is mounted between a left-right pair of bead portions 1, and ends of the carcass layer 4 are wound by being folded around bead cores 5 and a bead filler 6 from an inner side to an outer side of the tire.

In the tire tread portion 3, a belt layer 7 is provided along the entire periphery of the tire on the outer side of the carcass layer 4.

Additionally, rim cushions 8 are provided in parts of the bead portions 1 that are in contact with a rim.

The tire of the present invention can be produced by, for example, forming a tire tread portion by performing vulcanization or crosslinking at a temperature corresponding to the type and compounding ratio of the diene rubber, vulcanizing agent or crosslinking agent, and vulcanization or crosslinking accelerator used in the rubber compositions of the present invention.

Examples

The rubber composition for a tire tread of the present invention is described in detail below with reference to examples. However, the present invention is not limited to these examples.

Synthesis of Carboxynitrone

In a 2 L eggplant-shaped flask, methanol heated to 40° C. (900 mL) was placed, and then terephthalaldehydic acid represented by Formula (b-1) below (30.0 g) was added and dissolved. To this solution, a solution in which phenylhydroxylamine represented by Formula (a-1) below (21.8 g) was dissolved in methanol (100 mL) was added and stirred at room temperature for 19 hours. After the completion of stirring, a nitrone compound (carboxynitrone) represented by Formula (c-1) below was obtained by recrystallization from methanol (41.7 g). The yield was 86%.

[Chemical Formula 8]

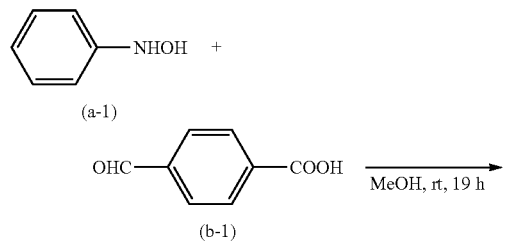

-continued (c-1) Y. 86%

Synthesis of Diphenylnitrone

In a 300 mL egg-plant shaped flask, benzaldehyde represented by Formula (b-2) below (42.45 g) and ethanol (10 mL) were placed, and then a solution in which phenylhydroxylamine represented by Formula (a-1) below (43.65 g) was dissolved in ethanol (70 mL) was added and stirred at room temperature for 22 hours. After the completion of stirring, diphenylnitrone (65.40 g) represented by Formula (c-2) below was obtained as white crystal by recrystallization from ethanol. The yield was 83%.

[Chemical Formula 9]

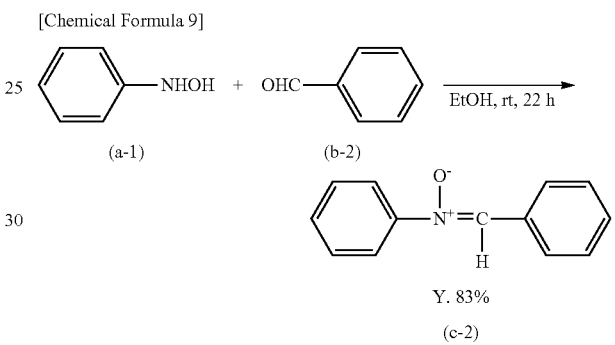

Synthesis of Carboxy-Modified BR 1 (Modified BR 1)

In a Banbury mixer at 120° C., a BR (trade name: Nipol BR1220, manufactured by Zeon Corporation) was added and masticated for 2 minutes. Then, 1 part by mass of the carboxynitrone synthesized as above was added per 100 parts by mass of BR and mixed at 160° C. for 5 minutes to modify the BR with the carboxynitrone. The obtained carboxy-modified BR 1 was used as the modified BR 1.

When NMR analysis was performed for the obtained modified BR 1 to determine the degree of modification, the degree of modification of the modified BR 1 was 0.17 mol %. Specifically, the degree of modification was determined as described below. The degree of modification was determined by measuring the peak area (derived from two protons adjacent to the carboxy group) at around 8.08 ppm via $^1$H-NMR analysis (CDCl$_3$, 400 MHz, TMS) for the BR before and after the modification, using CDCl$_3$ as a solvent. Note that the $^1$H-NMR analysis of the modified BR 1 was performed by using a sample obtained by dissolving the modified BR 1 in toluene, performing purification by methanol precipitation twice, and then drying under reduced pressure.

Synthesis of Carboxy-Modified BR 2 (Modified BR 2)

BR was modified with carboxynitrone in the same manner as in the synthesis of the modified BR 1 except for charging 2 parts by mass of carboxynitrone per 100 parts by mass of BR. The obtained carboxy-modified BR 2 was used as the modified BR 2.

When NMR analysis was performed for the obtained modified BR 2 to determine the degree of modification, the degree of modification of the modified BR 2 was 0.34 mol %. The method of determining the degree of modification was as described above.

Synthesis of Diphenyl-Modified BR 1 (Modified BR 3)

In a Banbury mixer at 120° C., a BR (trade name: Nipol BR1220, manufactured by Zeon Corporation) was added and masticated for 2 minutes. Then, 1 part by mass of the diphenylnitrone synthesized as above was added per 100 parts by mass of BR and mixed at 160° C. for 5 minutes to modify the BR with the diphenylnitrone. The obtained diphenyl-modified BR 1 was used as the modified BR 3.

When NMR analysis was performed for the obtained modified BR 3 to determine the degree of modification, the degree of modification of the modified BR 3 was 0.19 mol %. The method of determining the degree of modification was as described above.

Preparation of Microparticle-Containing Crosslinkable Polymer

Using a concentric biaxial mixer (manufactured by Inoue MFG., Inc.), 400 g of maleic acid-modified liquid polyisoprene rubber (Kuraprene LIR-403, manufactured by Kuraray Co., Ltd.; number average molecular weight: 34000), 120 g of process oil (Diana process oil PS-32, manufactured by Idemitsu Kosan Co., Ltd.), 16 g of oxazolidine compound (Hardener OZ, manufactured by Sumika Bayer Urethane Co., Ltd.), 1600 g of polyoxypropylene glycol having a terminal capped with a hydrolyzable silyl group (MS polymer S810, manufactured by Kaneka Corporation), and 5 g of water were stirred at a low speed of 36 rpm and a high speed dispersion of 600 rpm for 1 hour.

To this, 6 g of pluronic-type nonionic surfactant (Newpol PE-64, manufactured by Sanyo Chemical Industries, Ltd.) and 6 g of aminosilane (A1110, manufactured by Nippon Unicar Co., Ltd.) were then added, and a paste-like product (hereinafter, also referred to as "microparticle-containing crosslinkable polymer") was prepared by stirring at a low speed of 36 rpm and a high speed dispersion of 2000 rpm for 30 minutes.

When this paste-like product was observed using the laser microscope VK-8710 (manufactured by Keyence Corporation), it was confirmed that microparticles having a particle size of 5 to 40 μm (backbone: polyisoprene; crosslink: amide ester bonding) were produced and dispersed in polyoxypropylene glycol having a terminal capped with a hydrolyzable silyl group. Furthermore, as a result of subjecting this image to image processing and 3D profiling, the content (mass %) of the microparticles in the paste-like product was approximately 22%.

Preparation of Rubber Composition for Tire Tread

The components shown in Table 1 and Table 2 below were blended in the proportions (part by mass) shown in Table 1 and Table 2 below.

Specifically, the components shown in Table 1 and Table 2 below except the sulfur and the vulcanization accelerator were first mixed in a Banbury mixer at 80° C. for 5 minutes. Thereafter, the sulfur and the vulcanization accelerator were mixed using a roll to obtain a rubber composition for a tire tread of each of the examples and the comparative examples (hereinafter, "rubber composition for a tire tread" is also simply referred to as "rubber composition").

Production of Vulcanized Rubber Sheet

A vulcanized rubber sheet was prepared by press-vulcanizing each of the obtained (unvulcanized) rubber compositions for 15 minutes at 160° C. in a mold (15 cm×15 cm×0.2 cm).

Performance on Ice

Each produced vulcanized rubber sheet was measured for the loss tangent (tan δ (0° C.)) using a viscoelastic spectrometer (manufactured by Toyo Seiki Seisaku-sho, Ltd.) under the following conditions: 10% initial distortion, ±2% amplitude, 20 Hz frequency, and temperature of 0° C.

The obtained results were shown in Table 1 and Table 2 below as "performance on ice" as follows: the results in Table 1 below were expressed with the value of Comparative Example 1 expressed as an index of 100, and the results in Table 2 below were expressed with the value of Comparative Example 4 expressed as an index of 100. A larger index value indicates a larger tan δ (0° C.) and superior performance on ice.

Wear Resistance

Wear resistance test was performed in accordance with JIS K 6264-2:2005 using a Lambourn abrasion test machine (manufactured by Iwamoto Seisakusho Co. Ltd.) under the following conditions to measure wear mass: applied force: 4.0 kg/cm³ (=39 N); slip rate: 30%; duration of wear resistance test: 4 minutes; and test temperature: room temperature.

The test results were shown in Table 1 and Table 2 below as "wear resistance" as follows using the following equation. The results in Table 1 below were expressed with the measured value of Comparative Example 1 expressed as an index of 100, and the results in Table 2 below were expressed with the measured value of Comparative Example 4 expressed as an index of 100. A larger index indicates less amount of wear and better wear resistance.

Index=(amount of wear of test piece of Comparative Example 1 or Comparative Example 4/measured value)×100

In Table 1 and Table 2, "nitrone conversion amount" indicates the amount in terms of part by mass of the nitrone compound used in the synthesis of the modified polymer (modified BR 1, modified BR 2, or modified BR 3) relative to 100 parts by mass of the diene rubber. Note that, when carboxynitrone is used in the modification, the value is expressed as "CPN amount" which is synonymous with the converted CPN amount described above. Furthermore, when diphenylnitrone is used in the modification, the

TABLE 1

| Table 1 | | Comparative Example 1 | Comparative Example 2 | Comparative Example 3 | Example 1 | Example 2 | Example 3 |
|---|---|---|---|---|---|---|---|
| Diene rubber | NR | 50 | 50 | 50 | 50 | 50 | 50 |
| | BR | 50 | 20 | | 20 | | |
| | Modified BR 1 (carboxy-modified BR 1) | | | | 30 | 50 | |
| | Modified BR 2 (carboxy-modified BR 2) | | | | | | 50 |

TABLE 1-continued

| Table 1 | | Comparative Example 1 | Comparative Example 2 | Comparative Example 3 | Example 1 | Example 2 | Example 3 |
|---|---|---|---|---|---|---|---|
| | Modified BR 3 (diphenyl-modified BR 1) | | 30 | 50 | | | |
| | Thermally expandable microcapsule | 4 | 4 | 4 | 4 | 4 | 4 |
| | Microparticle-containing crosslinkable polymer | 10 | 10 | 10 | 10 | 10 | 10 |
| Other components | Carbon black | 35 | 35 | 35 | 35 | 35 | 35 |
| | Silica | 25 | 25 | 25 | 25 | 25 | 25 |
| | Silane coupling agent | 2 | 2 | 2 | 2 | 2 | 2 |
| | Stearic acid | 2 | 2 | 2 | 2 | 2 | 2 |
| | Wax | 2 | 2 | 2 | 2 | 2 | 2 |
| | Anti-aging agent | 2 | 2 | 2 | 2 | 2 | 2 |
| | Oil | 20 | 20 | 20 | 20 | 20 | 20 |
| | Zinc oxide | 4 | 4 | 4 | 4 | 4 | 4 |
| | Vulcanization accelerator | 1.5 | 1.5 | 1.5 | 1.5 | 1.5 | 1.5 |
| | Sulfur | 1.5 | 1.5 | 1.5 | 1.5 | 1.5 | 1.5 |
| Nitrone conversion amount | CPN amount (mol %) | | | | 0.3 | 0.5 | 1 |
| | DPN amount (mol %) | | 0.3 | 0.5 | | | |
| Evaluation results | Performance on ice | 100 | 100 | 101 | 101 | 101 | 102 |
| | Wear resistance: | 100 | 96 | 93 | 109 | 116 | 118 |

TABLE 2

| | | Comparative Example 4 | Example 4 |
|---|---|---|---|
| Diene rubber | NR | 50 | 50 |
| | BR | 50 | 20 |
| | Modified BR 1 (carboxy-modified BR 1) | | 30 |
| | Modified BR 2 (carboxy-modified BR 2) | | |
| | Modified BR 3 (diphenyl-modified BR 1) | | |
| | Thermally expandable microcapsule | 4 | 4 |
| | Microparticle-containing crosslinkable polymer | | |
| Other components | Carbon black | 35 | 35 |
| | Silica | 25 | 25 |
| | Silane coupling agent | 2 | 2 |
| | Stearic acid | 2 | 2 |
| | Wax | 2 | 2 |
| | Anti-aging agent | 2 | 2 |
| | Oil | 20 | 20 |
| | Zinc oxide | 4 | 4 |
| | Vulcanization accelerator | 1.5 | 1.5 |
| | Sulfur | 1.5 | 1.5 |
| Nitrone conversion amount | CPN amount (mol %) | | 0.3 |
| | DPN amount (mol %) | | |
| Evaluation results | Performance on ice | 100 | 103 |
| | Wear resistance | 100 | 110 |

The details of the components shown in Table 1 and Table 2 above are as follows.

NR: Natural rubber, STR 20

BR: Butadiene rubber; Nipol BR1220, manufactured by Zeon Corporation

Modified BR 1: Modified BR 1 synthesized as described above (carboxy-modified BR 1)

Modified BR 2: Modified BR 2 synthesized as described above (carboxy-modified BR 2)

Modified BR 3: Modified BR 3 synthesized as described above (diphenyl-modified BR 1)

Thermally expandable microcapsules: Matsumoto Microsphere F-100D (manufactured by Matsumoto Yushi-Seiyaku Co., Ltd.)

Microparticle-containing crosslinkable polymer: synthesized as described above

Carbon black: Show Black N339 (CTAB adsorption specific surface area: 90 m$^2$/g, manufactured by Cabot Japan K.K.)

Silica: ULTRASIL VN-3 (CTAB adsorption specific surface area: 155 m$^2$/g, manufactured by Evonik Degussa)

Silane coupling agent: Si69 (manufactured by Evonik Degussa)

Stearic acid: Stearic acid YR (manufactured by NOF Corporation)

Wax: Paraffin wax (manufactured by Ouchi Shinko Chemical Industrial Co., Ltd.)

Anti-aging agent: SANTOFLEX 6PPD (manufactured by Soltia Europe), N-phenyl-N'-(1,3-dimethylbutyl)-p-phenylenediamine Oil: Extract No. 4S (manufactured by Showa Shell Sekiyu K.K.)

Zinc oxide: Zinc Oxide III (manufactured by Seido Chemical Industry Co., Ltd.)

Vulcanization accelerator: Sanceller CM-G (manufactured by Sanshin Chemical Industry Co., Ltd.)

Sulfur: Oil treatment sulfur (manufactured by Karuizawa Refinery Ltd.)

As is clear from the evaluation results of Table 1, among systems containing the thermally expandable microcapsules and the microparticle-containing crosslinkable polymer, the case of using the carboxy-modified butadiene rubber (Examples 1 to 3) exhibited superior performance on ice and wear resistance compared to the case of using no carboxy-modified butadiene rubber (Comparative Examples 1 to 3).

As is clear from the comparison between Example 1 and Example 2, even better wear resistance was achieved by setting the content of the carboxy-modified butadiene rubber to 50 mass % or greater relative to the total mass of the diene rubber.

As is clear from the comparison between Example 2 and Example 3, even better performance on ice and wear resistance were achieved by setting the degree of modification of the carboxy-modified butadiene rubber to 0.2 mol % or greater.

As is clear from the evaluation results of Table 2, among systems containing the thermally expandable microcapsules but containing no microparticle-containing crosslinkable polymer, the case of using the carboxy-modified butadiene rubber (Example 4) exhibited superior performance on ice and wear resistance compared to the case of using no carboxy-modified butadiene rubber (Comparative Example 4).

REFERENCE SIGNS LIST

1 Bead portion
2 Sidewall portion
3 Tire tread portion
4 Carcass layer
5 Bead core
6 Bead filler
7 Belt layer
8 Rim cushion

The invention claimed is:

1. A rubber composition for a tire tread, the rubber composition comprising:
   100 parts by mass of a diene rubber (A) containing a modified butadiene rubber, and
   from 0.5 to 25 parts by mass of thermally expandable microcapsules (B);
   the modified butadiene rubber being obtained by modifying an unmodified butadiene rubber with a carboxy group-containing nitrone compound through a cycloaddition reaction between a double bond derived from a conjugated diene contained in the unmodified butadiene rubber and the carboxy group-containing nitrone compound; and
   a content of the modified butadiene rubber in the diene rubber (A) being from 20 to 65 mass %.

2. The rubber composition for a tire tread according to claim 1, further comprising:
   from 0.3 to 30 parts by mass of a crosslinkable oligomer or polymer (C) not compatible with the diene rubber (A), and
   from 0.1 to 12 parts by mass of three-dimensionally crosslinked microparticles (D) having an average particle diameter of 1 to 200 µm.

3. The rubber composition for a tire tread according to claim 2, wherein the microparticles (D) are microparticles in which an oligomer or polymer (d1) not compatible with the crosslinkable oligomer or polymer (C) is three-dimensionally crosslinked.

4. The rubber composition for a tire tread according to claim 3, wherein the oligomer or polymer (d1) is a polycarbonate-based, aliphatic, saturated hydrocarbon-based, acrylic, or plant-derived polymer or copolymer.

5. The rubber composition for a tire tread according to claim 4, wherein the crosslinkable oligomer or polymer (C) is a polyether-based, polyester-based, polyolefin-based, polycarbonate-based, acrylic, or plant-derived polymer or copolymer, and the oligomer or polymer (d1) is an aliphatic polymer or copolymer.

6. The rubber composition for a tire tread according to claim 3, wherein the crosslinkable oligomer or polymer (C) is a polyether-based, polyester-based, polyolefin-based, polycarbonate-based, aliphatic, saturated hydrocarbon-based, acrylic, or plant-derived polymer or copolymer.

7. The rubber composition for a tire tread according to claim 6, wherein the oligomer or polymer (d1) is a polycarbonate-based, aliphatic, saturated hydrocarbon-based, acrylic, or plant-derived polymer or copolymer.

8. The rubber composition for a tire tread according to claim 7, wherein the crosslinkable oligomer or polymer (C) is a polyether-based, polyester-based, polyolefin-based, polycarbonate-based, acrylic, or plant-derived polymer or copolymer, and
   the oligomer or polymer (d1) is an aliphatic polymer or copolymer.

9. The rubber composition for a tire tread according to claim 6, wherein the crosslinkable oligomer or polymer (C) is a polyether-based, polyester-based, polyolefin-based, polycarbonate-based, acrylic, or plant-derived polymer or copolymer, and
   the oligomer or polymer (d1) is an aliphatic polymer or copolymer.

10. The rubber composition for a tire tread according to claim 3, wherein the carboxy group-containing nitrone compound is a compound selected from the group consisting of N-phenyl-α-(4-carboxyphenyl)nitrone, N-phenyl-α-(3-carboxyphenyl)nitrone, N-phenyl-α-(2-carboxyphenyl)nitrone, N-(4-carboxyphenyl)-α-phenylnitrone, N-(3-carboxyphenyl)-α-phenylnitrone, and N-(2-carboxyphenyl)-α-phenylnitrone.

11. The rubber composition for a tire tread according to claim 2, wherein the crosslinkable oligomer or polymer (C) is a polyether-based, polyester-based, polyolefin-based, polycarbonate-based, aliphatic, saturated hydrocarbon-based, acrylic, or plant-derived polymer or copolymer.

12. The rubber composition for a tire tread according to claim 11, wherein the crosslinkable oligomer or polymer (C) is a polyether-based, polyester-based, polyolefin-based, polycarbonate-based, acrylic, or plant-derived polymer or copolymer, and
   the oligomer or polymer (d1) is an aliphatic polymer or copolymer.

13. The rubber composition for a tire tread according to claim 11, wherein the oligomer or polymer (d1) is a polycarbonate-based, aliphatic, saturated hydrocarbon-based, acrylic, or plant-derived polymer or copolymer.

14. The rubber composition for a tire tread according to claim 13, wherein the crosslinkable oligomer or polymer (C) is a polyether-based, polyester-based, polyolefin-based, polycarbonate-based, acrylic, or plant-derived polymer or copolymer, and
   the oligomer or polymer (d1) is an aliphatic polymer or copolymer.

15. The rubber composition for a tire tread according to claim 11, wherein the carboxy group-containing nitrone compound is a compound selected from the group consisting of N-phenyl-α-(4-carboxyphenyl)nitrone, N-phenyl-α-(3-carboxyphenyl)nitrone, N-phenyl-α-(2-carboxyphenyl)nitrone, N-(4-carboxyphenyl)-α-phenylnitrone, N-(3-carboxyphenyl)-α-phenylnitrone, and N-(2-carboxyphenyl)-α-phenylnitrone.

16. The rubber composition for a tire tread according to claim 2, wherein the carboxy group-containing nitrone compound is a compound selected from the group consisting of N-phenyl-α-(4-carboxyphenyl)nitrone, N-phenyl-α-(3-carboxyphenyl)nitrone, N-phenyl-α-(2-carboxyphenyl)nitrone, N-(4-carboxyphenyl)-α-phenylnitrone, N-(3-carboxyphenyl)-α-phenylnitrone, and N-(2-carboxyphenyl)-α-phenylnitrone.

17. The rubber composition for a tire tread according to claim 1, wherein the carboxy group-containing nitrone compound is a compound selected from the group consisting of N-phenyl-α-(4-carboxyphenyl)nitrone, N-phenyl-α-(3-carboxyphenyl)nitrone, N-phenyl-α-(2-carboxyphenyl)nitrone, N-(4-carboxyphenyl)-α-phenylnitrone, N-(3-carboxyphenyl)-α-phenylnitrone, and N-(2-carboxyphenyl)-α-phenylnitrone.

18. The rubber composition for a tire tread according to claim 1, wherein, when a proportion (mol %) of double bonds modified with the carboxy group-containing nitrone compound among all the double bonds derived from butadiene contained in the unmodified butadiene rubber is a degree of modification, the degree of modification of the modified butadiene rubber is from 0.02 to 4.0 mol %.

19. The rubber composition for a tire tread according to claim 1, wherein an amount of the carboxy group-containing nitrone compound used during the modification of the unmodified butadiene rubber is from 0.3 to 10 parts by mass per 100 parts by mass of the unmodified butadiene rubber.

20. A studless tire comprising the rubber composition for a tire tread described in claim 1 in a tire tread portion.

\* \* \* \* \*